US00PP11330P

United States Patent [19]

Anderson

[11] Patent Number: Plant 11,330

[45] Date of Patent: Apr. 4, 2000

[54] BLACK CURRANT PLANT NAMED 'BEN TIRRAN'

[75] Inventor: Malcolm M. Anderson, Dundee, United Kingdom

[73] Assignee: Scottish Crop Research Institute, Dundee, United Kingdom

[21] Appl. No.: 09/100,954

[22] Filed: Jun. 22, 1998

[51] Int. Cl.[7] ..... A01H 5/00

[52] U.S. Cl. ..... Plt./156

[58] Field of Search ..... Plt./156

[56] References Cited

U.S. PATENT DOCUMENTS

P.P. 9,889 5/1997 Anderson ..... Plt./156

*Primary Examiner*—Howard J. Locker
*Assistant Examiner*—Wendy A Baker
*Attorney, Agent, or Firm*—Burns, Doane, Swecker & Mathis, L.L.P

[57] ABSTRACT

A new and distinct cultivar of black currant (i.e., *Ribes nigrum* L.) is provided. The cultivar forms attractive very large deep black glossy berries in good yields that are well amenable to mechanical harvesting. A vigorous and compact growth habit commonly is exhibited. The new cultivar flowers very late and the berries also mature late in the season. Good resistance to American gooseberry mildew is exhibited. The new cultivar is well suited for consumption when freshly picked or can be canned to form jams, preserves, conserves, etc.

3 Drawing Sheets

SUMMARY OF THE INVENTION

The new black currant (i.e., *Ribes nigrum* L.) cultivar of the present invention was created during the course of a planned breeding program carried out during 1978 at the Scottish Crop Research Institute, Dundee, Scotland. The female parent (i.e., the seed parent) was the 'Ben Lomond' cultivar (non-patented in the United States). The male parent (i.e., the pollen parent) was the product of the complex crossing of 'Seabrooks Black', 'Amos Black' and the Ribesia species (all non-patented in the United States). The parentage of the new cultivar can be summarized as follows:

'Ben Lomond'×[('Seabrooks Black'×'Amos Black') ×('Seabrooks Black'×Ribesia species.)].

The original plant of the new cultivar was selected from the plants resulting from this cross and was found to exhibit:

(a) a late flowering propensity,
(b) a vigorous and upright growth habit that is well amenable to mechanical fruit harvest,
(c) the ability to bear large glossy deep black fully-ripened berries of good quality in high yields that mature very late in the season and are particularly well suited for fresh consumption and canning, and
(d) exhibits good resistance to American gooseberry mildew.

When compared to the parent 'Ben Lomond' cultivar, the new cultivar of the present invention commonly flowers approximately 7 to 8 days later, forms berries that commonly ripen approximately 3 to 7 days later and commonly are smaller in size, exhibits a more upright growth habit, forms leaves that are of a paler green coloration and are less rugose, and forms petioles that bear anthocyanin coloration substantially exclusively at the base.

The new cultivar can be grown to advantage while employing a standard planting density of approximately 7,400 plants/hectare. Ease of management is provided since the new cultivar commonly requires a reduced need for autumn pruning.

The new cultivar has been asexually reproduced by hardwood cuttings, softwood cuttings, single bud cuttings, and tissue culture at the Scottish Crop Research Institute, Dundee, Scotland. Such asexual reproduction has demonstrated that the characteristics of the new cultivar are stable and are transmitted without change through succeeding propagations. Additionally, the performance of the new cultivar has been evaluated at the National Fruit Trials held at Brogdale Experimental Horticulture Station, Faversham, Kent, United Kingdom, and at the Institute of Horticultural Plant Breeding, Balsgard, Sweden.

The new cultivar of the present invention has been named the 'Ben Tirran' cutlivar.

When plant material of the 'Ben Tirran' cultivar is subjected to RAPD fingerprinting using primer OPA-o6 GGTCCCTGAC, it is found to exhibit a bandmap which conforms its genetic distinctiveness as described in "RAPD fingerprinting of blackcurrant (*Ribes nigrum* L.) cultivars," by P. G. Lanham, R. M. Brennan, C. Hackett, and R. J. McNicol, appearing in *Theor. Appl. Genet.*, vol. 90, Pages 166 to 172 (1995), which is herein incorporated by reference.

BRIEF DESCRIPTION OF THE PHOTOGRAPHS

The accompanying photographs show typical specimens of the new cultivar in color as true as is reasonably possible to make the same in color illustrations of this character. The plants had been asexually reproduced by hardwood cuttings and were grown outdoors in breeding plots of the Scottish Crop Research Institute located at Dundee, Scotland.

DETAILED DESCRIPTION

Figure 1:
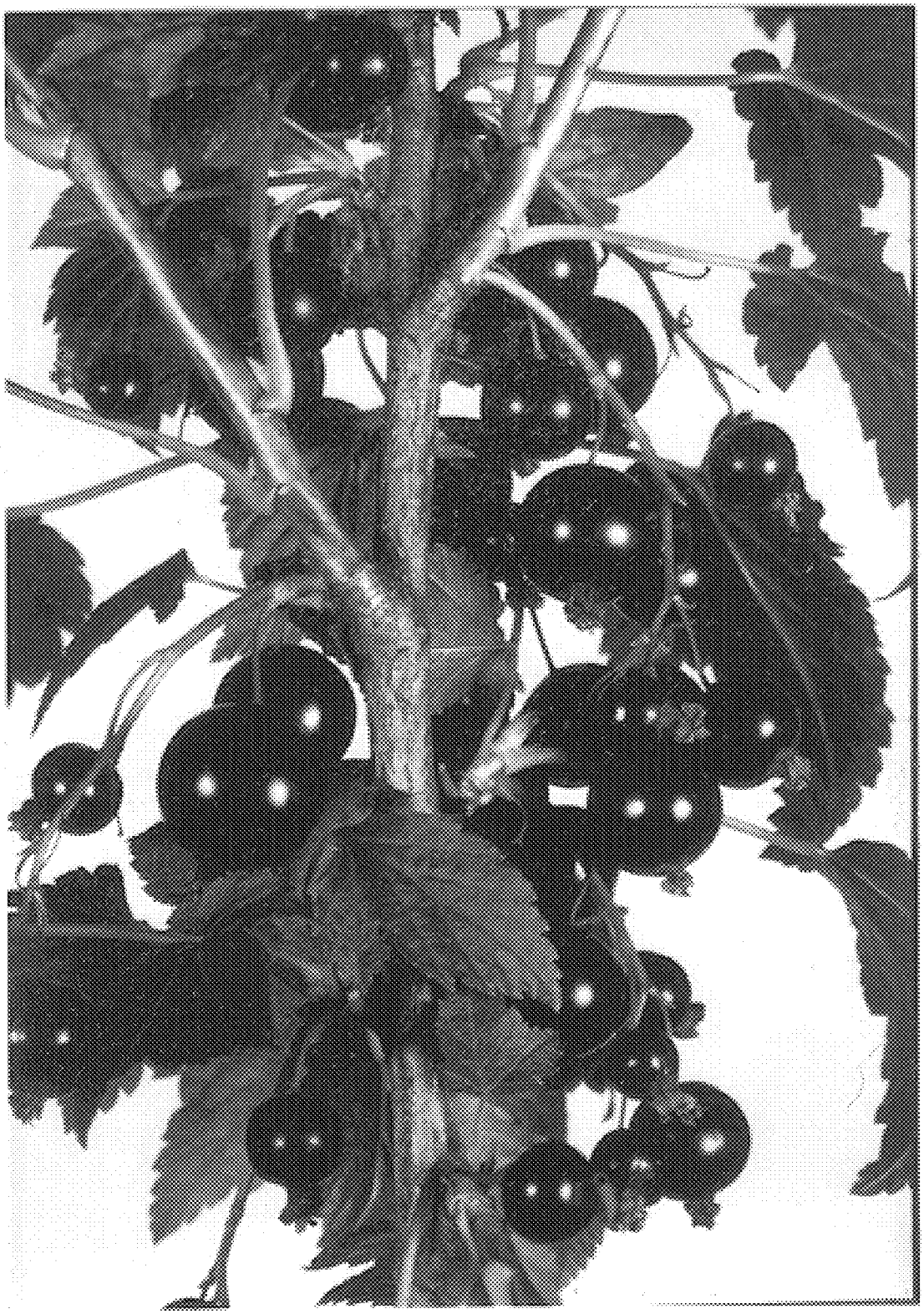
FIG. 1 illustrates a typical fruiting stem of the new variety wherein the deep black glossy fruit and the foliage are depicted.
Figure 2:
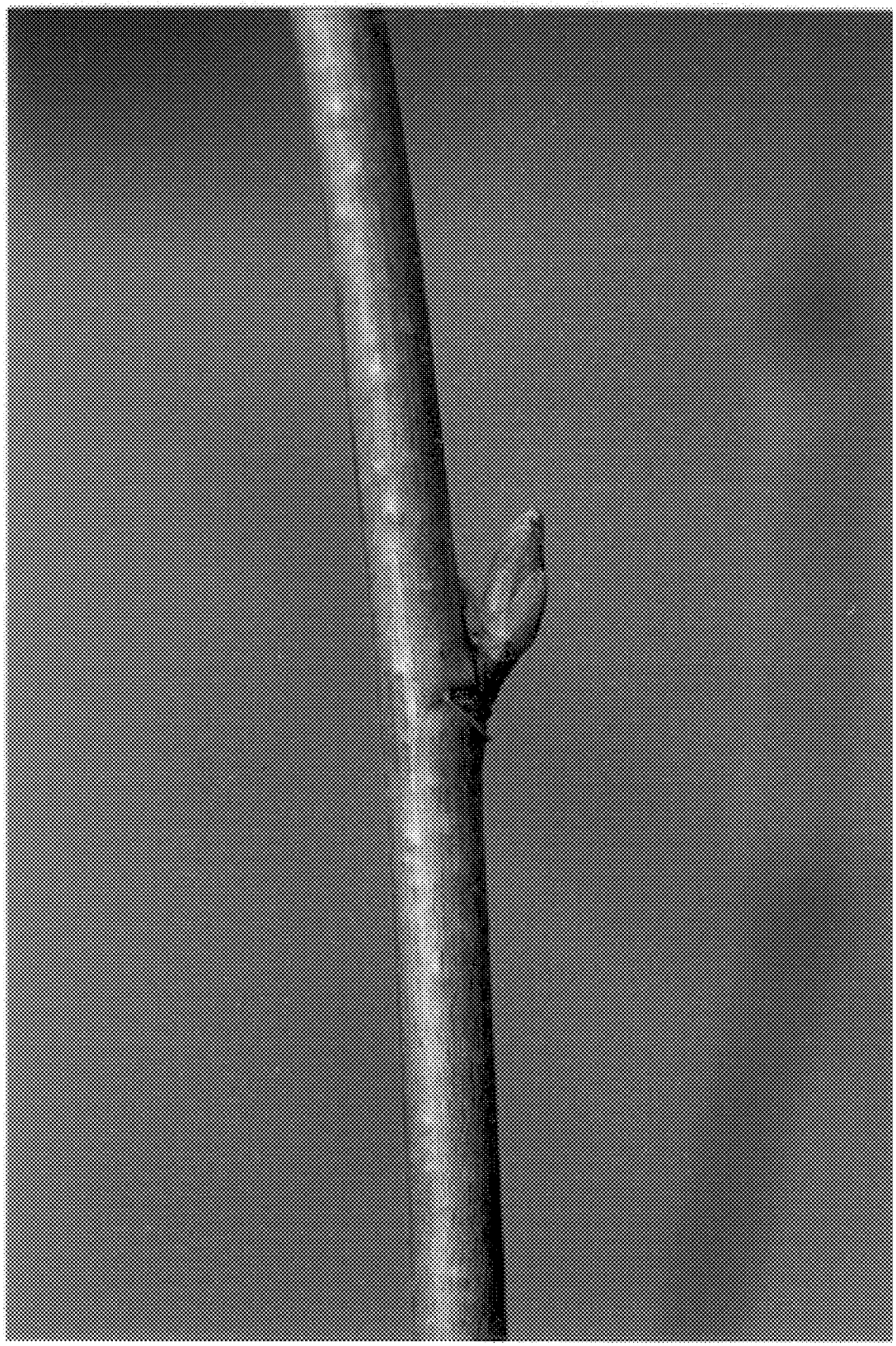
FIG. 2 illustrates a typical stem and long ovate dormant bud of the new cultivar.
Figure 3:
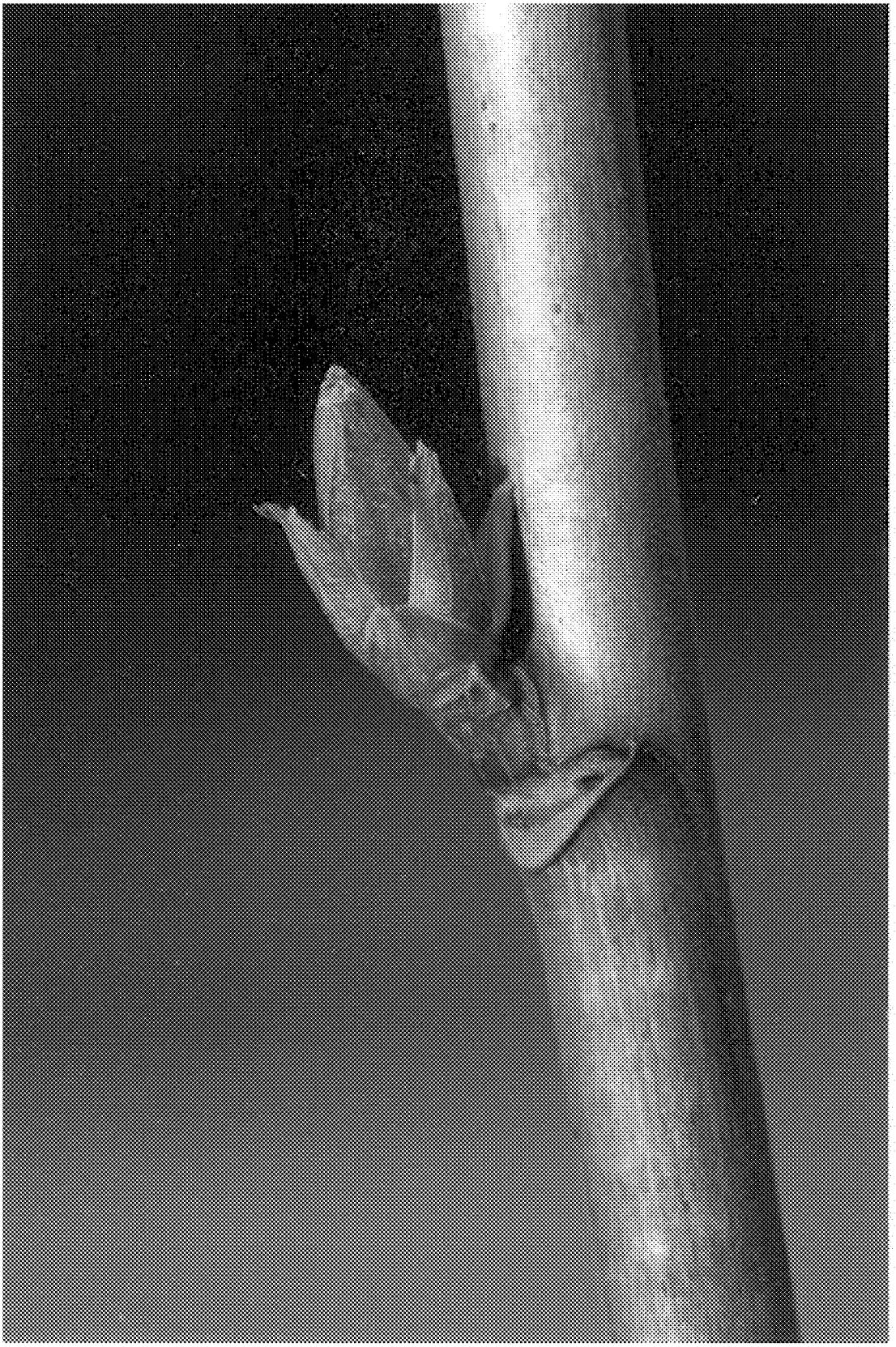
FIG. 3 illustrates a close-up view of a typical stem and bud of the new cultivar as the bud is in the process of opening.

The following is a detailed description of the new cultivar. The specimens described were grown at the Scottish Crop Research Institute, Dundee, Scotland, and at the National Fruit Trials held at the Brogdale Experimental Horticultural Station, Faversham, Kent, United Kingdom. The chart used in the identification of colors is that of The Royal Horticultural Society (R.H.S. Colour Chart). Other color terms are to be accorded their customary dictionary significance.

Plant:

*Growth habit.*—The growth habit is upright and is medium in size. The overall growth habit tends to be rounded. The branches may bend over slightly when carrying a full fruit crop, but will substantially return to their original upright position following harvest.

*Dimensions.*—Commonly approximately 1.2 m. in height and approximately 0.7 m. in width for a typical three year-old bush.

*Basal shoots.*—Numerous.

*Vigor.*—Strong with vigorous erect shoots are formed in moderate to high numbers.

Leaves:

*Leaf coloration.*—Commonly near Yellow-Green Group 144A, with some variation depending on specific growing conditions that are encountered. Is substantially the same on the upper and lower surfaces of the leaves. The coloration commonly is a paler green than that of the 'Ben Lomond' cultivar (non-patented in the United States).

*Leaf configuration.*—The base of the blade is open, the midrib has no curvature, and the terminal lobe is medium.

*Leaf size.*—The leaves possess three lobes and a cordate base. The leaf margins are serrate-dentate. Pubescence is absent. Medium, and typically approximately 13 cm. in length and approximately 6 to 10 cm. in width when mature.

*Petiole length.*—Approximately 2 to 3 cm. on average.

*Petiole coloration.*—Commonly Yellow-Green Group 144B, with some variation depending on specific growing conditions, and substantially without anthocyanin coloration. Red Group 40D only at the base.

*Petiole suface.*—Possesses moderate to sparse pubescence.

*Stem coloration.*—Commonly with varying shades of dark brown (as illustrated).

Flowers:

*Bud coloration.*—Yellow-Green Group 144B, with some variation depending on specific growing conditions. Overwintering buds are long-ovate, large and commonly without anthocyanin. The sepals are near Red Group 49D in coloration.

*Flowering date.*—Very late; commonly approximately May 5th for full flower at Kent, United Kingdom; and approximately 7 to 8 days after the 'Ben Lomond' cultivar. The exact flowering time for a given season is dependent upon the environmental conditions that are encountered.

*Flower configuration.*—Broadly campanulate, and commonly borne in groups of approximately 8 to 10 on racemes having a length of approximately 3 to 4 cm.

*Flower coloration.*—Off-white (Yellow-White Group 158B), with medium anthocyanin coloration on the sepal and ovary. The stems are Greyed-Orange Group 171C.

*Flower racemes.*—Medium in length, and commonly lax and drooping.

*Flower frequency.*—Commonly produced one or two racemes per bud and commonly with approximately 5 to 7 flowers on a primary raceme.

*Flower fragrance.*—None.

Fruit:

*Size.*—Large (generally larger than that of the 'Baldwin' cultivar (non-patented in the United States) and smaller than that of the 'Ben Lomond' cultivar. For instance, approximately 100 berries of the new cultivar commonly weight approximately 81.8 grams, compared to approximately 95 grams for the 'Ben Lomond' cultivar. The berries commonly measure approximately 0.6 to 0.9 cm. in diameter.

*Taste.*—Pleasant with an acid-sweet flavor.

*Configuration.*—Round (as illustrated).

*Consistency.*—Firm.

*Appearance.*—Glossy, and deep black that approaches Black Group 202A when fully ripe. The fruit coloration varies somewhat with the stage of ripeness as illustrated in FIG. 1. The fruit is attractive and is well presented on the bush. The fruit flesh is near transparent in appearance.

*Fruit ripening.*—Very late. Approximately 4 to 5 days after the 'Ben Lomond' cultivar and approximately 6 days later than the 'Ben Sarek' cultivar (non-patented in the United States) at the same location. Also, the ripening tends to be more even and uniform than that of the 'Ben Lomond' cultivar. The ripening date in a given season is influenced by environmental conditions that are encountered.

*Anthocyanin content.*—Using spectrophotometry at an absorbance of 515 nm. the value was fairly high at approximately 0.81. This compares to approximately 0.87 for the 'Ben Lomond' cultivar.

*Ascorbic acid content.*—Approximately 197 mg./100 g. were observed. This compares to 176 mg./100 g. for the 'Ben Lomond' cultivar. Accordingly the new cultivar has been observed to be superior to the 'Ben Lomond' cultivar with respect to ascorbic acid content.

*Yields.*—High yields, typically approximately 17 tonnes/hectare on average at most locations where testing has been carried out. The yields have been observed to be very consistent from year to year.

*Management and harvesting.*—Suitable for machine picking in view of upright growth habit and can be agronomically managed using conventional growing conditions with a reduced need for autumn pruning.

*Market.*—Excellent for consumption while fresh or for canning to produce jams, preserves, conserves, etc. The fruit is not ideally suited for juice production.

Disease and pest resistance: Good resistance to American gooseberry mildew (i.e., *Sphaerotheca morsuvae*). There appears to be average susceptibility to other black currant pests and diseases during observations to date.

Resistance to cold: Good tolerance to winter temperatures throughout Europe has been observed as well as reasonable tolerance to spring frosts.

I claim:

1. A new and distinct variety of black currant plant having the following combination of characteristics:

(a) a later flowering propensity,
(b) a vigorous and upright growth habit that is well amenable to mechanical fruit harvest,
(c) the ability to bear large glossy deep black fully-ripened berries of good quality in high yields that mature late in the season and are particularly well suited for fresh consumption and canning, and
(d) exhibits good resistance to American gooseberry mildew;

substantially as herein shown and described.

* * * * *